United States Patent [19]

Donetti et al.

[11] 4,259,253
[45] Mar. 31, 1981

[54] PROCESS FOR THE PREPARATION OF STEREOSPECIFIC TRANS, TRANS-FARNESYLACETIC ACID

[75] Inventors: Arturo Donetti, Milan; Enzo Cereda, Tortona; Elio Bellora, Milan, all of Italy

[73] Assignee: Istituto de Angeli S.p.A., Milan, Italy

[21] Appl. No.: 115,736

[22] Filed: Jan. 28, 1980

[51] Int. Cl.³ .................. C11C 1/04; C11D 13/00; C11C 1/00

[52] U.S. Cl. .................. 260/418; 260/413; 260/415; 260/417

[58] Field of Search ............. 260/417, 418, 413, 415

[56] References Cited

U.S. PATENT DOCUMENTS 3,928,403  12/1975  Fujita et al. ............ 260/410.9 N
4,028,385  6/1977   Fujita et al. ............ 260/410.9 R Primary Examiner—John F. Niebling
Attorney, Agent, or Firm—Hammond & Littell, Weissenberger & Muserlian

[57] ABSTRACT

A novel process for the preparation of pure trans, trans-farnesylacetic acid of the formula

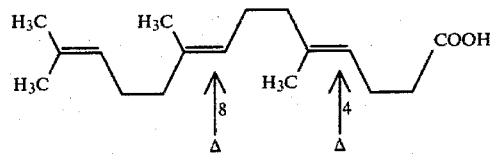

by recrystallization of a mixture of alkali metal salts of trans, trans- and cis, trans-farnesylacetic acid from an organic solvent, and conversion of the isolated alkali metal trans, trans-farnesylacetate into the free acid.

6 Claims, 4 Drawing Figures

PROCESS FOR THE PREPARATION OF STEREOSPECIFIC TRANS, TRANS-FARNESYLACETIC ACID

This invention relates to a novel process for the preparation of trans, trans-farnesylacetic acid [alternate nomenclature: trans(4), trans(8)-farnesylacetic acid or trans(4), trans(8)-5,9,13-trimethyl-4,8,12-tetradecatrienoic acid] by recrystallization of the potassium salt of the isomer mixture of trans(4), trans(8)- and cis(4)-trans(8)-farnesylacetic acid.

For the sake of brevity and simplicity, these isomeric forms of farnesylacetic acid are hereinafter referred simply as trans,trans- and cis,trans-farnesylacetic acid, respectively; they are represented by the following formulas:

trans(4), trans(8)-farnesylacetic acid:

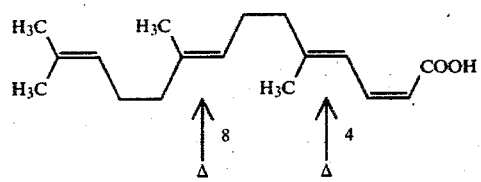

cis(4), trans(8)-farnesylacetic acid:

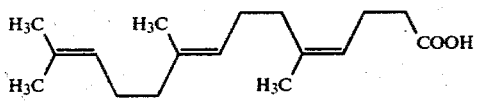

BACKGROUND OF THE INVENTION AND THE PRIOR ART

The mixture of the geranyl esters of these two farnesylacetic acid isomers is a useful product possessing anti-ulcerogenic activity, as is reported in Medicina Experimentalis 7, 171 (1962), which is widely used as a pharmaceutical at present. Since trans,trans-geranyl farnesylacetate is the predominant isomer in the trans,-trans/cis, trans mixture, it is therefore highly desirable to find a convenient method for the preparation of the pure form of this compound and/or its precursor, i.e. trans,trans-farnesylacetic acid (I).

Farnesylacetic acid and esters thereof may, in theory, occur in four stereoisomeric forms, due to the two double bonds in 4- and 8-position which are capable of forming cis,trans-geometric isomers. Besides the above-mentioned forms (I) and (II), there exist the two other possible isomeric forms, namely trans(4), cis(8)- and cis(4), cis (8)-farnesylacetic acid which correspond to the following formulas:

trans(4), cis(8)-farnesylacetic acid:

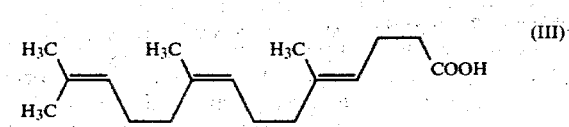

cis(4), cis(8)-farnesylacetic acid:

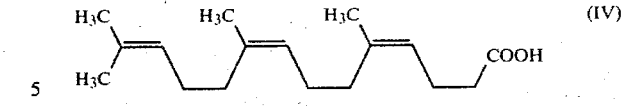

However, these two isomeric forms are only of scientific interest and have no economic significance, at present.

All four of the isomeric forms of farnesylacetic acid or their esters are obtained in admixture with each other if one starts, as usual, from a mixture of cis- and transnerodilol (see British Pat. No. 938 712 as well as U.S. Pat. No. 3,928,403).

Of course, the number of possible stereoisomers may be restricted from four to two, if one starts from only one isomer of nerolidol. In fact, the use of a starting nerolidol possessing a previously defined double bond geometry (trans or cis) leads to only one pair of isomers (I and II, or III and IV, respectively). However, since a second double bond is introduced by the subsequent reaction step, it is not possible to obtain pure trans,trans-farnesylacetic acid solely by the choice of a pure nerolidol isomer.

However, processes for production of trans,trans-farnesylacetic acid are already known. These are either based on the principle of stereospecific synthesis (Japanese Patent Application J 5-1029-437 of Teikoku Kagaku Sangyo) or the separation of isomers by fractional distillation (German Offenlegungsschrift No. 2,538,532). A process for the production of the geranyl esters by column-chromatography is also known [see Helv. chim. Acta 53, 1827 (1970)].

Yet all these known processes have serious disadvantages. Thus the process of sterospecific synthesis involves a laborious purification of the starting product, geranylacetone, via the semi-carbazone according to the method of Isler et al. (Helv. chim. Acta 39, 897 (1956). Besides, the process involves the use of expensive intermediate products, is complicated and represents a Wittig reaction, of which it is known (see Quart. Rev. 1964, 9, 255) that it will yield trans or cis isomers, depending upon the conditions applied, but that there remains much to be desired as far as the stereochemical purity of the product obtained is concerned.

The separation of isomers of farnesylacetic acid by fractional distillation in vacuo involves the use of a special equipment and, due to the close proximity of the boiling points of the components, requires critical working conditions.

The column-chromatographical separation of the geranyl esters is only suitable for work on a laboratory scale.

OBJECTS OF THE INVENTION

It is an object of the invention to provide a process for the production of pure trans,trans-farnesylacetic acid, at moderate cost and with high yields.

Other objects and advantages of the invention will become apparent as the description thereof proceeds.

DESCRIPTION OF THE INVENTION

We have discovered that the separation of trans,-trans- from cis,trans-farnesylacetic acid succeeds in a simple manner if a mixture of the two acids is converted into their higher alkali metal salts, for example, their potassium, rubidium and cesium salts, and the mixture of these stereoisomeric salts is then recrystallized from suitable organic solvents. For separation of the potassium salts, ethyl acetate, aliphatic or aromatic hydrocarbons (hexane, ligroin, petroleum ether, cyclohexane, benzene), ethers (dioxane, ethyl ether, tetrahydrofuran), ketones (acetone), lower aliphatic alcohols (ethanol, isopropanol) or chlorinated hydrocarbons (di-, tri- and tetrachloromethane) have proved to be suitable; especially favorable is the use of ethyl acetate. For separation of the stereoisomeric mixture of the two rubidium salts, ethers such as ethyl ether, tetrahydrofuran or dioxane, lipophilic hydrocarbons such as benzene, ligroin, carbon tetrachloride, chloroform or dichloromethane, esters (ethyl acetate) or ketones (acetone) may be used. The separation of the cesium salts succeeds preferably by means of ethers (ethyl ether, tetrahydrofuran, dioxane), lipophilic hydrocarbons (ligroin, hexane), esters (ethyl acetate) or ketones (acetone).

The separation is based on the fact that the aforementioned salts, in particular the potassium salts of trans, trans- and cis,trans-farnesylacetic acid, show a remarkable difference in solubility. In organic solvents the former is always significantly less soluble than the latter. Due to this surprising difference, the trans,trans-isomer may be separated by simple recrystallization, preferably of the potassium salt of the isomeric mixture.

A mixture of the two stereoisomeric salts mentioned above may either be obtained by direct salt formation of the isomeric mixture of the two farnesylacetic acids or by hydrolysis of a corresponding mixture of esters (for example of trans, trans- and cis,trans-farnesylacetic acid, methyl, ethyl or geranyl esters with an alkali metal hydroxide, for example, with potassium hydroxide).

Recrystallization from a number of solvents delivers a good yield of the trans,trans-farnesylacetic acid of excellent stereospecifity.

The following examples illustrate the present invention and will enable others skilled in the art to understand it more completely. It should be understood, however, that the invention is not limited solely to the particular examples given below.

EXAMPLE 1

Powdered potassium hydroxide (0.056 mol) was added to a solution of 15 gm (0.056 mol) of an isomeric mixture of farnesylacetic acid (trans,trans 70.67%; cis,-trans 29.33% pursuant to gas-chromatographic determination). The clear solution thus obtained was evaporated to dryness and yielded 17 gm of the potassium salts of the isomeric mixture in the form of a wax-like, white solid. This mixture was recrystallized from ethylacetate and yielded a potassium salt of the single trans,-trans-isomer as colorless crystals. This salt was dissolved in water, and the solution was acidified with 10% sulfuric acid and then extracted with ethyl ether. The ether extract was washed with water until it remained neutral, and was then dried over anhydrous magnesium sulfate. After evaporation of the solvent, 8.17 gm of trans,trans-farnesylacetic acid (77% yield of the actual content of trans-isomer in the original mixture) were obtained.

EXAMPLE 2

The same separation could be achieved starting from the isomeric mixture (trans,trans/cis,trans) of the corresponding esters (methyl, ethyl or geranyl).

Hydrolysis of these esters in ethanol with potassium hydroxide (molar ratio of the esters to potassium hydroxide 1:2) for three hours at reflux yielded, after evaporation of the solvent and the work-up procedure described above, trans,trans-farnesylacetic acid. Other solvents that may be used for recrystallization of the potassium salt of the isomeric mixture are: hexane, ligroin, petroleum ether, cyclohexane, dioxane, benzene, ethyl ether, tetrahydrofuran, acetone, ethanol, isopropanol, dichloromethane, chloroform or carbon tetrachloride.

The physical-chemical characteristics of the trans,-trans-farnesylacetic acid obtained in accordance with the foregoing examples are shown in the attached drawings, of which FIG. 1 is a gas-chromatogram of the trans,trans-farnesylacetic acid ($\simeq$99%);

Analysis: Calculated for $C_{17}H_{28}O_2$: C-77.22%; H-10.67%. C-77.33%; H-10.54%.

Figure 1:
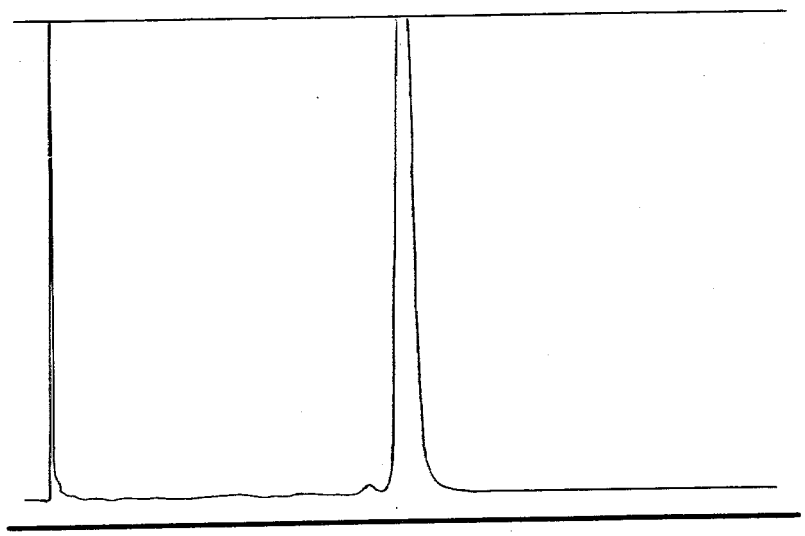
Figure 2:
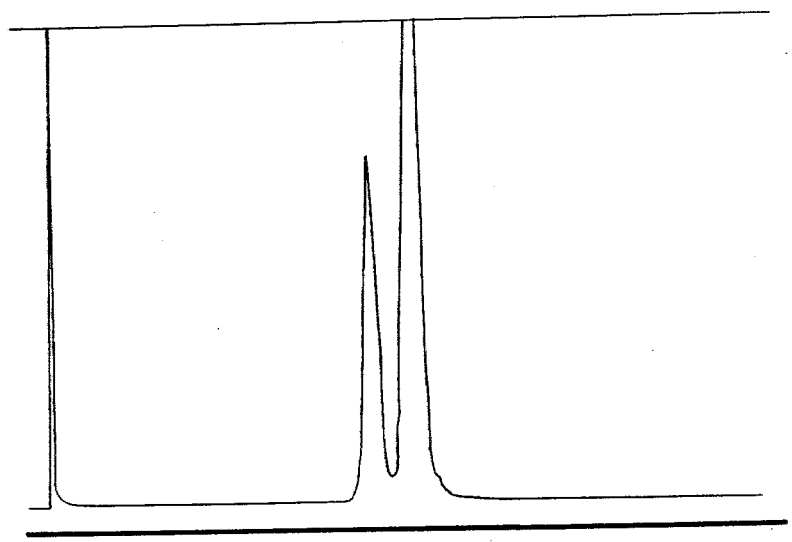
FIG. 2 is a gas-chromatogram of an isomeric mixture of trans,trans- and cis,trans-farnesylacetic acid (70:30)

The gas-chromatographic analysis of this material (as methyl ester obtained with diazomethane) showed that it consists of $\simeq$99% of the trans,trans-isomer of the isomeric mixture (see FIG. 1 in comparison to FIG. 2 showing the gas-chromatogram).

Figure 3:
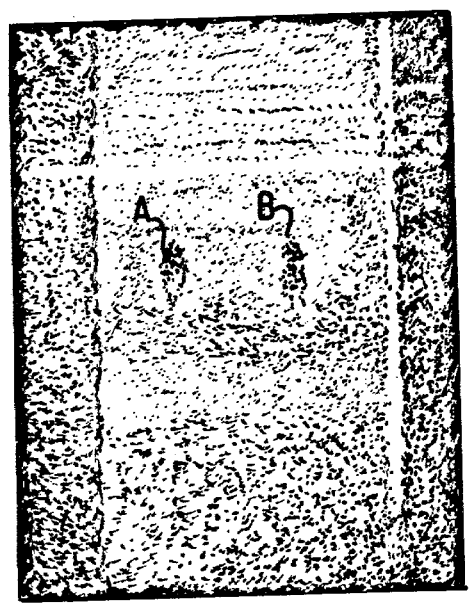
FIG. 3 is a thin-layer chromatogram of trans,trans-farnesylacetic acid (spot A) and of the isomeric mixture referred to in FIG. 2.

The thin-layer chromatogram on silver nitratesilicagel plates using 20% toluene in ethyl acetate as the mobile phase, showed one spot ($R_f\simeq0.54$) that corresponded to the trans,trans-isomer (see FIG. 3, spot A in comparison to spot B that corresponds to the isomeric mixture).

Figure 4:
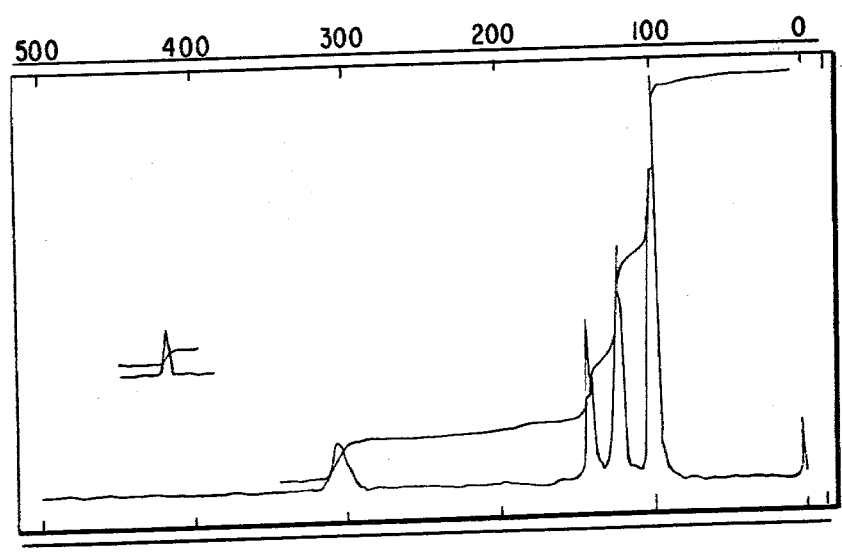
FIG. 4 is the NMR-spectrum of trans,trans-farnesylacetic acid.

The NMR-spectrum (see FIG. 4) agreed with the assumed structure (see formula I).

EXAMPLE 3

7.42 gm (0.053 mol) of rubidium hydroxide dihydrate were added to a solution of 14.55 gm (0.053 mol) of the isomeric mixture of trans,trans- and cis,trans-farnesylacetic acid in 65 ml of 95% ethanol. The clear solution was evaporated to dryness and yielded 18 gm of the rubidium salt as a wax-like product.

The latter was recrystallized from acetone and yielded the rubidium salt of the single trans,trans-isomer as colorless crystals. This salt was worked up as described in Example 1 and yielded trans,trans-farnesylacetic acid (71% yield for the actual content of trans, trans-isomer in the original mixture).

Other solvents suitable for crystallizing the rubidium salt of the isomeric mixture include: ligroin, benzene, ethyl ether, dioxane, tetrahydrofuran, ethyl acetate, dichloromethane, chloroform and carbon tetrachloride.

EXAMPLE 4

A mixture of trans,trans- and cis,trans-farnesylacetic acid (11.37 gm, 0.043 mol) dissolved in 25 ml of 95% ethanol, was treated with 6.45 gm (0.043 mol) of cesium hydroxide.

The obtained solution was evaporated to dryness and yielded 16.9 gm of the cesium salt as wax. This wax was recrystallized from ethyl acetate and yielded the single trans,trans-isomer as colorless crystals. The corresponding acid was obtained as described in Example 1. Yield: 61% of the actual content of the trans,trans-isomer in the original mixture.

Other solvents suitable for crystallizing the cesium salt of the isomeric mixture include: hexane, ligroin, ethyl ether, dioxane, tetrahydrofuran and acetone.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A process for the isolation of substantially pure trans,trans-farnesylacetic acid from an isomeric mixture of trans,trans- and cis,trans-farnesylacetic acid or an ester thereof, which comprises converting the components of said isomeric mixture into their higher alkali metal salts, separating the salt of trans,trans-farnesylacetic acid by recrystallization from an organic solvent, and converting the isolated salt of trans,trans-farnesylacetic acid into the free acid by acidification.

2. A process of claim 1, wherein the conversion of the isomeric mixture of esters into the isomeric mixture of alkali metal salts is effected by hydrolysis with an alkali metal hydroxide.

3. A process of claim 2, where said alkali metal hydroxide is potassium hydroxide.

4. A process of claim 1, wherein said organic solvent is a lower aliphatic hydrocarbon, an alcohol, an ether, a ketone or a chlorinated hydrocarbon.

5. A process of claim 1, wherein said organic solvent is ethyl acetate.

6. A process of claim 1, wherein said higher alkali metal is potassium, rubidium or cesium.

* * * * *